United States Patent [19]
Cohen et al.

[11] Patent Number: 5,891,719
[45] Date of Patent: Apr. 6, 1999

[54] IKAP NUCLEIC ACIDS

[75] Inventors: Lucie Cohen; Patrick Baeuerle, both of South San Francisco, Calif.

[73] Assignee: Tularik Inc., South San Francisco, Calif.

[21] Appl. No.: 971,244

[22] Filed: Nov. 16, 1997

[51] Int. Cl.$^6$ .............. C12N 5/10; C12N 15/12; C12N 15/11; C07K 14/47
[52] U.S. Cl. .............. 435/325; 435/252.3; 435/254.11; 435/69.1; 536/23.5; 536/23.1; 536/24.3; 536/24.31; 530/300; 530/350
[58] Field of Search .................. 435/69.1, 320, 435/325, 252.3, 254.11; 536/23.5, 23.1, 24.3, 24.31; 530/350, 351, 300

[56] References Cited

PUBLICATIONS

Hillier, et al. Accession No. W52507, Database: Genebank--EST, May 31, 1996.
Darnell, et al. in Molecular Cell Biology. p. 641, Scientific American Books, Inc., New York, NY, 1986.
GenBank Accession No. H19711, Hillier et al., accessed Oct. 28, 1998, Jul. 1995.
GenBank Accession No. H15327, Hillier et al., accessed Oct. 28, 1998, Jun. 1995.
GenBank Accession AA455598, "aa17d06.rl" Soares NhH-MPu S1 *Homo sapeins* cDNA clone 813515 5', accessed 04 Nov. 1998, Jun. 1997.
GenBank Accession AA324126, EST27019 cerebellum II *Homo sapeins* cDNA 5' end, accessed 04 Nov. 1998, Apr. 1997.
GenBank Accession AA478782, zv20c02.sl Soares NhH-MPu S1 *Homo sapeins* cDNA clone 754178 3', accessed 04 Nov. 1998, Aug. 1997.
GenBank Accession AA478782, zv20c02.rl Soares NhH-MPu S1 *Homo sapeins* cDNA clone 754178 5', accessed 04 Nov. 1998, Aug. 1997.
Adams et al., Initial assessment of human gene diversity and expression patterns based on 83 million nucleotides of cDNA sequence, Nature 377 (Supp.):3–174, pp. 3–17, Sept. 1995.

*Primary Examiner*—Lila Feisee
*Assistant Examiner*—Claire M. Kaufman
*Attorney, Agent, or Firm*—Richard Aron Osman

[57] ABSTRACT

The invention provides methods and compositions relating to IKAP proteins which regulate cellular signal transduction and transcriptional activation, and related nucleic acids. The polypeptides may be produced recombinantly from transformed host cells from the disclosed IKAP encoding nucleic acids or purified from human cells. The invention provides isolated IKAP hybridization probes and primers capable of specifically hybridizing with the disclosed IKAP genes, IKAP-specific binding agents such as specific antibodies, and methods of making and using the subject compositions in diagnosis, therapy and in the biopharmaceutical industry.

46 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 3999 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..3996

( x i ) SEQUENCE DESCRIPTION: SEQ ID NO:1:

```
ATG  CGA  AAT  CTG  AAA  TTA  TTT  CGG  ACC  CTG  GAG  TTC  AGG  GAT  ATT  CAA           48
Met  Arg  Asn  Leu  Lys  Leu  Phe  Arg  Thr  Leu  Glu  Phe  Arg  Asp  Ile  Gln
 1              5                        10                      15

GGT  CCA  GGG  AAT  CCT  CAG  TGC  TTC  TCT  CTC  CGA  ACT  GAA  CAG  GGG  ACG           96
Gly  Pro  Gly  Asn  Pro  Gln  Cys  Phe  Ser  Leu  Arg  Thr  Glu  Gln  Gly  Thr
                  20                      25                      30

GTG  CTC  ATT  GGT  TCA  GAA  CAT  GGC  CTG  ATA  GAA  GTA  GAC  CCT  GTC  TCA          144
Val  Leu  Ile  Gly  Ser  Glu  His  Gly  Leu  Ile  Glu  Val  Asp  Pro  Val  Ser
              35                      40                      45

AGA  GAA  GTG  AAA  AAT  GAA  GTT  TCT  TTG  GTG  GCA  GAA  GGC  TTT  CTT  CCA          192
Arg  Glu  Val  Lys  Asn  Glu  Val  Ser  Leu  Val  Ala  Glu  Gly  Phe  Leu  Pro
     50                      55                      60

GAG  GAT  GGA  AGT  GGC  CGC  ATT  GTT  GGT  GTT  CAG  GAC  TTG  CTG  GAT  CAG          240
Glu  Asp  Gly  Ser  Gly  Arg  Ile  Val  Gly  Val  Gln  Asp  Leu  Leu  Asp  Gln
 65                      70                      75                      80

GAG  TCT  GTG  TGT  GTG  GCC  ACA  GCC  TCT  GGA  GAC  GTC  ATA  CTC  TGC  AGT          288
Glu  Ser  Val  Cys  Val  Ala  Thr  Ala  Ser  Gly  Asp  Val  Ile  Leu  Cys  Ser
                  85                      90                      95

CTC  AGC  ACA  CAA  CAG  CTG  GAG  TGT  GTT  GGG  AGT  GTA  GCC  AGT  GGT  ATC          336
Leu  Ser  Thr  Gln  Gln  Leu  Glu  Cys  Val  Gly  Ser  Val  Ala  Ser  Gly  Ile
              100                     105                     110

TCT  GTT  ATG  AGT  TGG  AGT  CCT  GAC  CAA  GAG  CTG  GTG  CTT  CTT  GCC  ACA          384
Ser  Val  Met  Ser  Trp  Ser  Pro  Asp  Gln  Glu  Leu  Val  Leu  Leu  Ala  Thr
              115                     120                     125

GGT  CAA  CAG  ACC  CTG  ATT  ATG  ATG  ACA  AAA  GAT  TTT  GAG  CCA  ATC  CTG          432
Gly  Gln  Gln  Thr  Leu  Ile  Met  Met  Thr  Lys  Asp  Phe  Glu  Pro  Ile  Leu
     130                     135                     140

GAG  CAG  CAG  ATC  CAT  CAG  GAT  GAT  TTT  GGT  GAA  AGC  AAG  TTT  ATC  ACT          480
Glu  Gln  Gln  Ile  His  Gln  Asp  Asp  Phe  Gly  Glu  Ser  Lys  Phe  Ile  Thr
145                     150                     155                     160

GTT  GGA  TGG  GGT  AGG  AAG  GAG  ACA  CAG  TTC  CAT  GGA  TCA  GAA  GGC  AGA          528
Val  Gly  Trp  Gly  Arg  Lys  Glu  Thr  Gln  Phe  His  Gly  Ser  Glu  Gly  Arg
                  165                     170                     175

CAA  GCA  GCT  TTT  CAG  ATG  CAA  ATG  CAT  GAG  TCT  GCT  TTG  CCC  TGG  GAT          576
Gln  Ala  Ala  Phe  Gln  Met  Gln  Met  His  Glu  Ser  Ala  Leu  Pro  Trp  Asp
              180                     185                     190

GAC  CAT  AGA  CCA  CAA  GTT  ACC  TGG  CGG  GGG  GAT  GGA  CAG  TTT  TTT  GCT          624
Asp  His  Arg  Pro  Gln  Val  Thr  Trp  Arg  Gly  Asp  Gly  Gln  Phe  Phe  Ala
              195                     200                     205
```

| | | | | | | | | | | | | | | | | |
|---|---|---|---|---|---|---|---|---|---|---|---|---|---|---|---|---|
| GTG | AGT | GTT | GTT | TGC | CCA | GAA | ACA | GGG | GCT | CGG | AAG | GTC | AGA | GTG | TGG | 672 |
| Val | Ser | Val | Val | Cys | Pro | Glu | Thr | Gly | Ala | Arg | Lys | Val | Arg | Val | Trp | |
| | 210 | | | | 215 | | | | | 220 | | | | | | |
| AAC | CGA | GAG | TTT | GCT | TTG | CAG | TCA | ACC | AGT | GAG | CCT | GTG | GCA | GGA | CTG | 720 |
| Asn | Arg | Glu | Phe | Ala | Leu | Gln | Ser | Thr | Ser | Glu | Pro | Val | Ala | Gly | Leu | |
| 225 | | | | | 230 | | | | | 235 | | | | | 240 | |
| GGA | CCA | GCC | CTG | GCT | TGG | AAA | CCC | TCA | GGC | AGT | TTG | ATT | GCA | TCT | ACA | 768 |
| Gly | Pro | Ala | Leu | Ala | Trp | Lys | Pro | Ser | Gly | Ser | Leu | Ile | Ala | Ser | Thr | |
| | | | | 245 | | | | | 250 | | | | | 255 | | |
| CAA | GAT | AAA | CCC | AAC | CAG | CAG | GAT | ATT | GTG | TTT | TTT | GAG | AAA | AAT | GGA | 816 |
| Gln | Asp | Lys | Pro | Asn | Gln | Gln | Asp | Ile | Val | Phe | Phe | Glu | Lys | Asn | Gly | |
| | | | 260 | | | | | 265 | | | | | 270 | | | |
| CTC | CTT | CAT | GGA | CAC | TTT | ACA | CTT | CCC | TTC | CTT | AAA | GAT | GAG | GTT | AAG | 864 |
| Leu | Leu | His | Gly | His | Phe | Thr | Leu | Pro | Phe | Leu | Lys | Asp | Glu | Val | Lys | |
| | | 275 | | | | | 280 | | | | | 285 | | | | |
| GTA | AAT | GAC | TTG | CTC | TGG | AAT | GCA | GAT | TCC | TCT | GTG | CTT | GCA | GTC | CGG | 912 |
| Val | Asn | Asp | Leu | Leu | Trp | Asn | Ala | Asp | Ser | Ser | Val | Leu | Ala | Val | Arg | |
| | 290 | | | | | 295 | | | | | 300 | | | | | |
| CTG | GAA | GAC | CTT | CAG | AGA | GAA | AAA | AGC | TCC | ATT | CCG | AAA | ACC | TGT | GTT | 960 |
| Leu | Glu | Asp | Leu | Gln | Arg | Glu | Lys | Ser | Ser | Ile | Pro | Lys | Thr | Cys | Val | |
| 305 | | | | | 310 | | | | | 315 | | | | | 320 | |
| CAG | CTC | TGG | ACT | GTT | GGA | AAC | TAT | CAC | TGG | TAT | CTC | AAG | CAA | AGT | TTA | 1008 |
| Gln | Leu | Trp | Thr | Val | Gly | Asn | Tyr | His | Trp | Tyr | Leu | Lys | Gln | Ser | Leu | |
| | | | | 325 | | | | | 330 | | | | | 335 | | |
| TCC | TTC | AGC | ACC | TGT | GGG | AAG | AGC | AAG | ATT | GTG | TCT | CTG | ATG | TGG | GAC | 1056 |
| Ser | Phe | Ser | Thr | Cys | Gly | Lys | Ser | Lys | Ile | Val | Ser | Leu | Met | Trp | Asp | |
| | | | 340 | | | | | 345 | | | | | 350 | | | |
| CCT | GTG | ACC | CCA | TAC | CGG | CTG | CAT | GTT | CTC | TGT | CAG | GGC | TGG | CAT | TAC | 1104 |
| Pro | Val | Thr | Pro | Tyr | Arg | Leu | His | Val | Leu | Cys | Gln | Gly | Trp | His | Tyr | |
| | | 355 | | | | | 360 | | | | | 365 | | | | |
| CTC | GCC | TAT | GAT | TGG | CAC | TGG | ACG | ACT | GAC | CGG | AGC | GTG | GGA | GAT | AAT | 1152 |
| Leu | Ala | Tyr | Asp | Trp | His | Trp | Thr | Thr | Asp | Arg | Ser | Val | Gly | Asp | Asn | |
| | 370 | | | | | 375 | | | | | 380 | | | | | |
| TCA | AGT | GAC | TTG | TCC | AAT | GTG | GCT | GTC | ATT | GAT | GGA | AAC | AGG | GTG | TTG | 1200 |
| Ser | Ser | Asp | Leu | Ser | Asn | Val | Ala | Val | Ile | Asp | Gly | Asn | Arg | Val | Leu | |
| 385 | | | | | 390 | | | | | 395 | | | | | 400 | |
| GTG | ACA | GTC | TTC | CGG | CAG | ACT | GTG | GTT | CCG | CCT | CCC | ATG | TGC | ACC | TAC | 1248 |
| Val | Thr | Val | Phe | Arg | Gln | Thr | Val | Val | Pro | Pro | Pro | Met | Cys | Thr | Tyr | |
| | | | | 405 | | | | | 410 | | | | | 415 | | |
| CAA | CTG | CTG | TTC | CCA | CAC | CCT | GTG | AAT | CAA | GTC | ACA | TTC | TTA | GCA | CAC | 1296 |
| Gln | Leu | Leu | Phe | Pro | His | Pro | Val | Asn | Gln | Val | Thr | Phe | Leu | Ala | His | |
| | | | 420 | | | | | 425 | | | | | 430 | | | |
| CCT | CAA | AAG | AGT | AAT | GAC | CTT | GCT | GTT | CTA | GAT | GCC | AGT | AAC | CAG | ATT | 1344 |
| Pro | Gln | Lys | Ser | Asn | Asp | Leu | Ala | Val | Leu | Asp | Ala | Ser | Asn | Gln | Ile | |
| | | 435 | | | | | 440 | | | | | 445 | | | | |
| TCT | GTT | TAT | AAA | TGT | GGT | GAT | TGT | CCA | AGT | GCT | GAC | CCT | ACA | GTG | AAA | 1392 |
| Ser | Val | Tyr | Lys | Cys | Gly | Asp | Cys | Pro | Ser | Ala | Asp | Pro | Thr | Val | Lys | |
| | 450 | | | | | 455 | | | | | 460 | | | | | |
| CTG | GGA | GCT | GTG | GGT | GGA | AGT | GGA | TTT | AAA | GTT | TGC | CTT | AGA | ACT | CCT | 1440 |
| Leu | Gly | Ala | Val | Gly | Gly | Ser | Gly | Phe | Lys | Val | Cys | Leu | Arg | Thr | Pro | |
| 465 | | | | | 470 | | | | | 475 | | | | | 480 | |
| CAT | TTG | GAA | AAG | AGA | TAC | AAA | ATC | CAG | TTT | GAG | AAT | AAT | GAA | GAT | CAA | 1488 |
| His | Leu | Glu | Lys | Arg | Tyr | Lys | Ile | Gln | Phe | Glu | Asn | Asn | Glu | Asp | Gln | |
| | | | | 485 | | | | | 490 | | | | | 495 | | |
| GAT | GTA | AAC | CCG | CTG | AAA | CTA | GGC | CTT | CTC | ACT | TGG | ATT | GAA | GAA | GAC | 1536 |
| Asp | Val | Asn | Pro | Leu | Lys | Leu | Gly | Leu | Leu | Thr | Trp | Ile | Glu | Glu | Asp | |
| | | | 500 | | | | | 505 | | | | | 510 | | | |
| GTC | TTC | CTG | GCT | GTA | AGC | CAC | AGT | GAG | TTC | AGC | CCC | CGG | TCT | GTC | ATT | 1584 |
| Val | Phe | Leu | Ala | Val | Ser | His | Ser | Glu | Phe | Ser | Pro | Arg | Ser | Val | Ile | |
| | | 515 | | | | | 520 | | | | | 525 | | | | |

```
CAC  CAT  TTG  ACT  GCA  GCT  TCT  TCT  GAG  ATG  GAT  GAA  GAG  CAT  GGA  CAG    1632
His  His  Leu  Thr  Ala  Ala  Ser  Ser  Glu  Met  Asp  Glu  Glu  His  Gly  Gln
          530                 535                 540

CTC  AAT  GTC  AGT  TCA  TCT  GCA  GCG  GTG  GAT  GGG  GTC  ATA  ATC  AGT  CTA    1680
Leu  Asn  Val  Ser  Ser  Ser  Ala  Ala  Val  Asp  Gly  Val  Ile  Ile  Ser  Leu
545                      550                 555                      560

TGT  TGC  AAT  TCC  AAG  ACC  AAG  TCA  GTA  GTA  TTA  CAG  CTG  GCT  GAT  GGC    1728
Cys  Cys  Asn  Ser  Lys  Thr  Lys  Ser  Val  Val  Leu  Gln  Leu  Ala  Asp  Gly
                    565                      570                      575

CAG  ATA  TTT  AAG  TAC  CTT  TGG  GAG  TCA  CCT  TCT  CTG  GCT  ATT  AAA  CCA    1776
Gln  Ile  Phe  Lys  Tyr  Leu  Trp  Glu  Ser  Pro  Ser  Leu  Ala  Ile  Lys  Pro
               580                      585                      590

TGG  AAG  AAC  TCT  GGT  GGA  TTT  CCT  GTT  CGG  TTT  CCT  TAT  CCA  TGC  ACC    1824
Trp  Lys  Asn  Ser  Gly  Gly  Phe  Pro  Val  Arg  Phe  Pro  Tyr  Pro  Cys  Thr
          595                      600                      605

CAG  ACC  GAA  TTG  GCC  ATG  ATT  GGA  GAA  GAG  GAA  TGT  GTC  CTT  GGT  CTG    1872
Gln  Thr  Glu  Leu  Ala  Met  Ile  Gly  Glu  Glu  Glu  Cys  Val  Leu  Gly  Leu
     610                      615                      620

ACT  GAC  AGG  TGT  CGC  TTT  TTC  ATC  AAT  GAC  ATT  GAG  GTT  GCG  TCA  AAT    1920
Thr  Asp  Arg  Cys  Arg  Phe  Phe  Ile  Asn  Asp  Ile  Glu  Val  Ala  Ser  Asn
625                      630                      635                      640

ATC  ACG  TCA  TTT  GCA  GTA  TAT  GAT  GAG  TTT  TTA  TTG  TTG  ACA  ACC  CAT    1968
Ile  Thr  Ser  Phe  Ala  Val  Tyr  Asp  Glu  Phe  Leu  Leu  Leu  Thr  Thr  His
                    645                      650                      655

TCC  CAT  ACC  TGC  CAG  TGT  TTT  TGC  CTG  AGG  GAT  GCT  TCA  TTT  AAA  ACA    2016
Ser  His  Thr  Cys  Gln  Cys  Phe  Cys  Leu  Arg  Asp  Ala  Ser  Phe  Lys  Thr
               660                      665                      670

TTA  CAG  GCC  GGC  CTG  AGC  AGC  AAT  CAT  GTG  TCC  CAT  GGG  GAA  GTT  CTG    2064
Leu  Gln  Ala  Gly  Leu  Ser  Ser  Asn  His  Val  Ser  His  Gly  Glu  Val  Leu
          675                      680                      685

CGG  AAA  GTG  GAG  AGG  GGT  TCA  CGG  ATT  GTC  ACT  GTT  GTG  CCC  CAG  GAC    2112
Arg  Lys  Val  Glu  Arg  Gly  Ser  Arg  Ile  Val  Thr  Val  Val  Pro  Gln  Asp
     690                      695                      700

ACA  AAG  CTT  GTA  TTA  CAG  ATG  CCA  AGG  GGA  AAC  TTA  GAA  GTT  GTT  CAT    2160
Thr  Lys  Leu  Val  Leu  Gln  Met  Pro  Arg  Gly  Asn  Leu  Glu  Val  Val  His
705                      710                      715                      720

CAT  CGA  GCC  CTG  GTT  TTA  GCT  CAG  ATT  CGG  AAG  TGG  TTG  GAC  AAA  CTT    2208
His  Arg  Ala  Leu  Val  Leu  Ala  Gln  Ile  Arg  Lys  Trp  Leu  Asp  Lys  Leu
                    725                      730                      735

ATG  TTT  AAA  GAG  GCA  TTT  GAA  TGC  ATG  AGA  AAG  CTG  AGA  ATC  AAT  CTC    2256
Met  Phe  Lys  Glu  Ala  Phe  Glu  Cys  Met  Arg  Lys  Leu  Arg  Ile  Asn  Leu
               740                      745                      750

AAT  CCG  ATT  TAT  GAT  CAT  AAC  CCT  AAG  GTG  TTT  CTT  GGA  AAT  GTG  GAA    2304
Asn  Pro  Ile  Tyr  Asp  His  Asn  Pro  Lys  Val  Phe  Leu  Gly  Asn  Val  Glu
          755                      760                      765

ACC  TTC  ATT  AAA  CAG  ATA  GAT  TCT  GTG  AAT  CAT  ATT  AAC  TTG  TTT  TTT    2352
Thr  Phe  Ile  Lys  Gln  Ile  Asp  Ser  Val  Asn  His  Ile  Asn  Leu  Phe  Phe
     770                      775                      780

ACA  GAA  TTG  AAA  GAA  GAA  GAT  GTC  ACG  AAG  ACC  ATG  TAC  CCT  GCA  CCA    2400
Thr  Glu  Leu  Lys  Glu  Glu  Asp  Val  Thr  Lys  Thr  Met  Tyr  Pro  Ala  Pro
785                      790                      795                      800

GTT  ACC  AGC  AGT  GTC  TAC  CTG  TCC  AGG  GAT  CCT  GAC  GGG  AAT  AAA  ATA    2448
Val  Thr  Ser  Ser  Val  Tyr  Leu  Ser  Arg  Asp  Pro  Asp  Gly  Asn  Lys  Ile
                    805                      810                      815

GAC  CTT  GTC  TGC  GAT  GCT  ATG  AGA  GCA  GTC  ATG  GAG  AGC  ATA  AAT  CCT    2496
Asp  Leu  Val  Cys  Asp  Ala  Met  Arg  Ala  Val  Met  Glu  Ser  Ile  Asn  Pro
               820                      825                      830

CAT  AAA  TAC  TGC  CTA  TCC  ATA  CTT  ACA  TCT  CAT  GTA  AAG  AAG  ACA  ACC    2544
His  Lys  Tyr  Cys  Leu  Ser  Ile  Leu  Thr  Ser  His  Val  Lys  Lys  Thr  Thr
          835                      840                      845
```

| | | | | | | | | | | | | | | | | |
|---|---|---|---|---|---|---|---|---|---|---|---|---|---|---|---|---|
| CCA | GAA | CTG | GAA | ATT | GTA | CTG | CAA | AAA | GTA | CAC | GAG | CTT | CAA | GGA | AAT | 2592 |
| Pro | Glu | Leu | Glu | Ile | Val | Leu | Gln | Lys | Val | His | Glu | Leu | Gln | Gly | Asn | |
| 850 | | | | | 855 | | | | | 860 | | | | | | |
| GCT | CCC | TCT | GAT | CCT | GAT | GCT | GTG | AGT | GCT | GAA | GAG | GCC | TTG | AAA | TAT | 2640 |
| Ala | Pro | Ser | Asp | Pro | Asp | Ala | Val | Ser | Ala | Glu | Glu | Ala | Leu | Lys | Tyr | |
| 865 | | | | | 870 | | | | | 875 | | | | | 880 | |
| TTG | CTG | CAT | CTG | GTA | GAT | GTT | AAT | GAA | TTA | TAT | GAT | CAT | TCT | CTT | GGC | 2688 |
| Leu | Leu | His | Leu | Val | Asp | Val | Asn | Glu | Leu | Tyr | Asp | His | Ser | Leu | Gly | |
| | | | | 885 | | | | | 890 | | | | | 895 | | |
| ACC | TAT | GAC | TTT | GAT | TTG | GTC | CTC | ATG | GTA | GCT | GAG | AAG | TCA | CAG | AAG | 2736 |
| Thr | Tyr | Asp | Phe | Asp | Leu | Val | Leu | Met | Val | Ala | Glu | Lys | Ser | Gln | Lys | |
| | | | 900 | | | | | 905 | | | | | 910 | | | |
| GAT | CCC | AAA | GAA | TAT | CTT | CCA | TTT | CTT | AAT | ACA | CTT | AAG | AAA | ATG | GAA | 2784 |
| Asp | Pro | Lys | Glu | Tyr | Leu | Pro | Phe | Leu | Asn | Thr | Leu | Lys | Lys | Met | Glu | |
| | | 915 | | | | | 920 | | | | | 925 | | | | |
| ACT | AAT | TAT | CAG | CGG | TTT | ACT | ATA | GAC | AAA | TAC | TTG | AAA | CGA | TAT | GAA | 2832 |
| Thr | Asn | Tyr | Gln | Arg | Phe | Thr | Ile | Asp | Lys | Tyr | Leu | Lys | Arg | Tyr | Glu | |
| 930 | | | | | 935 | | | | | 940 | | | | | | |
| AAA | GCC | ATT | GGC | CAC | CTC | AGC | AAA | TGT | GGA | CCT | GAG | TAC | TTC | CCA | GAA | 2880 |
| Lys | Ala | Ile | Gly | His | Leu | Ser | Lys | Cys | Gly | Pro | Glu | Tyr | Phe | Pro | Glu | |
| 945 | | | | | 950 | | | | | 955 | | | | | 960 | |
| TGC | TTA | AAC | TTG | ATA | AAA | GAT | AAA | AAC | TTG | TAT | AAC | GAA | GCT | CTG | AAG | 2928 |
| Cys | Leu | Asn | Leu | Ile | Lys | Asp | Lys | Asn | Leu | Tyr | Asn | Glu | Ala | Leu | Lys | |
| | | | | 965 | | | | | 970 | | | | | 975 | | |
| TTA | TAT | TCA | CCA | AGC | TCA | CAA | CAG | TAC | CAG | GAT | ATC | AGC | ATT | GCT | TAT | 2976 |
| Leu | Tyr | Ser | Pro | Ser | Ser | Gln | Gln | Tyr | Gln | Asp | Ile | Ser | Ile | Ala | Tyr | |
| | | | 980 | | | | | 985 | | | | | 990 | | | |
| GGG | GAG | CAC | CTG | ATG | CAG | GAG | CAC | ATG | TAT | GAG | CCA | GCG | GGG | CTC | ATG | 3024 |
| Gly | Glu | His | Leu | Met | Gln | Glu | His | Met | Tyr | Glu | Pro | Ala | Gly | Leu | Met | |
| | | 995 | | | | | 1000 | | | | | 1005 | | | | |
| TTT | GCC | CGT | TGC | GGT | GCC | CAC | GAG | AAA | GCT | CTC | TCA | GCC | TTT | CTC | ACA | 3072 |
| Phe | Ala | Arg | Cys | Gly | Ala | His | Glu | Lys | Ala | Leu | Ser | Ala | Phe | Leu | Thr | |
| | 1010 | | | | | 1015 | | | | | 1020 | | | | | |
| TGT | GGC | AAC | TGG | AAG | CAA | GCC | CTC | TGT | GTG | GCA | GCC | CAG | CTT | AAC | TTT | 3120 |
| Cys | Gly | Asn | Trp | Lys | Gln | Ala | Leu | Cys | Val | Ala | Ala | Gln | Leu | Asn | Phe | |
| 1025 | | | | | 1030 | | | | | 1035 | | | | | 1040 | |
| ACC | AAA | GAC | CAG | CTG | GTG | GGC | CTC | GGC | AGA | ACT | CTG | GCA | GGA | AAG | CTG | 3168 |
| Thr | Lys | Asp | Gln | Leu | Val | Gly | Leu | Gly | Arg | Thr | Leu | Ala | Gly | Lys | Leu | |
| | | | | 1045 | | | | | 1050 | | | | | 1055 | | |
| GTT | GAG | CAG | AGG | AAG | CAC | ATT | GAT | GCG | GCC | ATG | GTT | TTG | GAA | GAG | TGT | 3216 |
| Val | Glu | Gln | Arg | Lys | His | Ile | Asp | Ala | Ala | Met | Val | Leu | Glu | Glu | Cys | |
| | | | 1060 | | | | | 1065 | | | | | 1070 | | | |
| GCC | CAG | GAT | TAT | GAA | GAA | GCT | GTG | CTC | TTG | CTG | TTA | GAA | GGA | GCT | GCC | 3264 |
| Ala | Gln | Asp | Tyr | Glu | Glu | Ala | Val | Leu | Leu | Leu | Leu | Glu | Gly | Ala | Ala | |
| | | 1075 | | | | | 1080 | | | | | 1085 | | | | |
| TGG | GAA | GAA | GCT | TTG | AGG | CTG | GTA | TAC | AAA | TAT | AAC | AGA | CTG | GAT | ATT | 3312 |
| Trp | Glu | Glu | Ala | Leu | Arg | Leu | Val | Tyr | Lys | Tyr | Asn | Arg | Leu | Asp | Ile | |
| | 1090 | | | | | 1095 | | | | | 1100 | | | | | |
| ATA | GAA | ACC | AAC | GTA | AAG | CCT | TCC | ATT | TTA | GAA | GCC | AGA | AAA | AAT | TAT | 3360 |
| Ile | Glu | Thr | Asn | Val | Lys | Pro | Ser | Ile | Leu | Glu | Ala | Gln | Lys | Asn | Tyr | |
| 1105 | | | | | 1110 | | | | | 1115 | | | | | 1120 | |
| ATG | GCA | TTT | CTG | GAC | TCT | CAG | ACA | GCC | ACA | TTC | AGT | CGC | CAC | AAG | AAA | 3408 |
| Met | Ala | Phe | Leu | Asp | Ser | Gln | Thr | Ala | Thr | Phe | Ser | Arg | His | Lys | Lys | |
| | | | | 1125 | | | | | 1130 | | | | | 1135 | | |
| CGT | TTA | TTG | GTA | GTT | CGA | GAG | CTC | AAG | GAG | CAA | GCC | CAG | CAG | GCA | GGT | 3456 |
| Arg | Leu | Leu | Val | Val | Arg | Glu | Leu | Lys | Glu | Gln | Ala | Gln | Gln | Ala | Gly | |
| | | | 1140 | | | | | 1145 | | | | | 1150 | | | |
| CTG | GAT | GAT | GAG | GTA | CCC | CAC | GGG | CAA | GAG | TCA | GAC | CTC | TTC | TCT | GAA | 3504 |
| Leu | Asp | Asp | Glu | Val | Pro | His | Gly | Gln | Glu | Ser | Asp | Leu | Phe | Ser | Glu | |
| | | 1155 | | | | | 1160 | | | | | 1165 | | | | |

| | | | | | | | | | | | | | | | | |
|---|---|---|---|---|---|---|---|---|---|---|---|---|---|---|---|---|
|ACT|AGC|AGT|GTC|GTG|AGT|GGC|AGT|GAG|ATG|AGT|GGC|AAA|TAC|TCC|CAT|3552|
|Thr|Ser|Ser|Val|Val|Ser|Gly|Ser|Glu|Met|Ser|Gly|Lys|Tyr|Ser|His| |
| | |1170| | | |1175| | | |1180| | | | | | |
|AGT|AAC|TCC|AGG|ATA|TCA|GCG|AGA|TCA|TCC|AAG|AAT|CGC|CGA|AAA|GCG|3600|
|Ser|Asn|Ser|Arg|Ile|Ser|Ala|Arg|Ser|Ser|Lys|Asn|Arg|Arg|Lys|Ala| |
|1185| | | | |1190| | | | |1195| | | | |1200| |
|GAG|CGG|AAG|AAG|CAC|AGC|CTC|AAA|GAA|GGC|AGT|CCG|CTG|GAG|GAC|CTG|3648|
|Glu|Arg|Lys|Lys|His|Ser|Leu|Lys|Glu|Gly|Ser|Pro|Leu|Glu|Asp|Leu| |
| | | | |1205| | | | |1210| | | | |1215| | |
|GCC|CTC|CTG|GAG|GCA|CTG|AGT|GAA|GTG|GTG|CAG|AAC|ACT|GAA|AAC|CTG|3696|
|Ala|Leu|Leu|Glu|Ala|Leu|Ser|Glu|Val|Val|Gln|Asn|Thr|Glu|Asn|Leu| |
| | | |1220| | | | |1225| | | | |1230| | | |
|AAA|GAT|GAA|GTA|TAC|CAT|ATT|TTA|AAG|GTA|CTC|TTT|CTC|TTT|GAG|TTT|3744|
|Lys|Asp|Glu|Val|Tyr|His|Ile|Leu|Lys|Val|Leu|Phe|Leu|Phe|Glu|Phe| |
| | |1235| | | | |1240| | | | |1245| | | | |
|GAT|GAA|CAA|GGA|AGG|GAA|TTA|CAG|AAG|GCC|TTT|GAA|GAT|ACG|CTG|CAG|3792|
|Asp|Glu|Gln|Gly|Arg|Glu|Leu|Gln|Lys|Ala|Phe|Glu|Asp|Thr|Leu|Gln| |
| | |1250| | | | |1255| | | | |1260| | | | |
|TTG|ATG|GAA|AGG|TCA|CTT|CCA|GAA|ATT|TGG|ACT|CTT|ACT|TAC|CAG|CAG|3840|
|Leu|Met|Glu|Arg|Ser|Leu|Pro|Glu|Ile|Trp|Thr|Leu|Thr|Tyr|Gln|Gln| |
|1265| | | | |1270| | | | |1275| | | | |1280| |
|AAT|TCA|GCT|ACC|CCG|GTT|CTA|GGT|CCC|AAT|TCT|ACT|GCA|AAT|AGT|ATC|3888|
|Asn|Ser|Ala|Thr|Pro|Val|Leu|Gly|Pro|Asn|Ser|Thr|Ala|Asn|Ser|Ile| |
| | | |1285| | | | |1290| | | | |1295| | | |
|ATG|GCA|TCT|TAT|CAG|CAA|CAG|AAG|ACT|TCG|GTT|CCT|GTT|CTT|GAT|GCT|3936|
|Met|Ala|Ser|Tyr|Gln|Gln|Gln|Lys|Thr|Ser|Val|Pro|Val|Leu|Asp|Ala| |
| | | |1300| | | | |1305| | | | |1310| | | |
|GAG|CTT|TTT|ATA|CCA|CCA|AAG|ATC|AAC|AGA|AGA|ACC|CAG|TGG|AAG|CTG|3984|
|Glu|Leu|Phe|Ile|Pro|Pro|Lys|Ile|Asn|Arg|Arg|Thr|Gln|Trp|Lys|Leu| |
| | |1315| | | | |1320| | | | |1325| | | | |
|AGC|CTG|CTA|GAC|TGA| | | | | | | | | | | |3999|
|Ser|Leu|Leu|Asp| | | | | | | | | | | | | |
| | |1330| | | | | | | | | | | | | | |

(2) INFORMATION FOR SEQ ID NO:2:

(i) SEQUENCE CHARACTERISTICS:
    (A) LENGTH: 1332 amino acids
    (B) TYPE: amino acid
    (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
|Met|Arg|Asn|Leu|Lys|Leu|Phe|Arg|Thr|Leu|Glu|Phe|Arg|Asp|Ile|Gln|
|1| | | |5| | | | |10| | | | |15|
|Gly|Pro|Gly|Asn|Pro|Gln|Cys|Phe|Ser|Leu|Arg|Thr|Glu|Gln|Gly|Thr|
| | | |20| | | | |25| | | | |30| |
|Val|Leu|Ile|Gly|Ser|Glu|His|Gly|Leu|Ile|Glu|Val|Asp|Pro|Val|Ser|
| | |35| | | | |40| | | | |45| | |
|Arg|Glu|Val|Lys|Asn|Glu|Val|Ser|Leu|Val|Ala|Glu|Gly|Phe|Leu|Pro|
| |50| | | | |55| | | | |60| | | |
|Glu|Asp|Gly|Ser|Gly|Arg|Ile|Val|Gly|Val|Gln|Asp|Leu|Leu|Asp|Gln|
|65| | | | |70| | | | |75| | | | |80|
|Glu|Ser|Val|Cys|Val|Ala|Thr|Ala|Ser|Gly|Asp|Val|Ile|Leu|Cys|Ser|
| | | | |85| | | | |90| | | | |95| |
|Leu|Ser|Thr|Gln|Gln|Leu|Glu|Cys|Val|Gly|Ser|Val|Ala|Ser|Gly|Ile|
| | | |100| | | | |105| | | | |110| | |
|Ser|Val|Met|Ser|Trp|Ser|Pro|Asp|Gln|Glu|Leu|Val|Leu|Leu|Ala|Thr|
| | |115| | | | |120| | | | |125| | | |

-continued

| | | | | | | | | | | | | | |
|---|---|---|---|---|---|---|---|---|---|---|---|---|---|
| Gly | Gln | Gln | Thr | Leu | Ile | Met | Met | Thr | Lys | Asp | Phe | Glu | Pro | Ile | Leu |
| | 130 | | | | | 135 | | | | | 140 | | |
| Glu | Gln | Gln | Ile | His | Gln | Asp | Asp | Phe | Gly | Glu | Ser | Lys | Phe | Ile | Thr |
| 145 | | | | | 150 | | | | | 155 | | | | | 160 |
| Val | Gly | Trp | Gly | Arg | Lys | Glu | Thr | Gln | Phe | His | Gly | Ser | Glu | Gly | Arg |
| | | | | 165 | | | | | 170 | | | | | 175 | |
| Gln | Ala | Ala | Phe | Gln | Met | Gln | Met | His | Glu | Ser | Ala | Leu | Pro | Trp | Asp |
| | | | 180 | | | | | 185 | | | | | 190 | | |
| Asp | His | Arg | Pro | Gln | Val | Thr | Trp | Arg | Gly | Asp | Gly | Gln | Phe | Phe | Ala |
| | | 195 | | | | | 200 | | | | | 205 | | | |
| Val | Ser | Val | Val | Cys | Pro | Glu | Thr | Gly | Ala | Arg | Lys | Val | Arg | Val | Trp |
| | 210 | | | | | 215 | | | | | 220 | | | | |
| Asn | Arg | Glu | Phe | Ala | Leu | Gln | Ser | Thr | Ser | Glu | Pro | Val | Ala | Gly | Leu |
| 225 | | | | | 230 | | | | | 235 | | | | | 240 |
| Gly | Pro | Ala | Leu | Ala | Trp | Lys | Pro | Ser | Gly | Ser | Leu | Ile | Ala | Ser | Thr |
| | | | | 245 | | | | | 250 | | | | | 255 | |
| Gln | Asp | Lys | Pro | Asn | Gln | Gln | Asp | Ile | Val | Phe | Phe | Glu | Lys | Asn | Gly |
| | | | 260 | | | | | 265 | | | | | 270 | | |
| Leu | Leu | His | Gly | His | Phe | Thr | Leu | Pro | Phe | Leu | Lys | Asp | Glu | Val | Lys |
| | | 275 | | | | | 280 | | | | | 285 | | | |
| Val | Asn | Asp | Leu | Leu | Trp | Asn | Ala | Asp | Ser | Ser | Val | Leu | Ala | Val | Arg |
| | 290 | | | | | 295 | | | | | 300 | | | | |
| Leu | Glu | Asp | Leu | Gln | Arg | Glu | Lys | Ser | Ser | Ile | Pro | Lys | Thr | Cys | Val |
| 305 | | | | | 310 | | | | | 315 | | | | | 320 |
| Gln | Leu | Trp | Thr | Val | Gly | Asn | Tyr | His | Trp | Tyr | Leu | Lys | Gln | Ser | Leu |
| | | | | 325 | | | | | 330 | | | | | 335 | |
| Ser | Phe | Ser | Thr | Cys | Gly | Lys | Ser | Lys | Ile | Val | Ser | Leu | Met | Trp | Asp |
| | | | 340 | | | | | 345 | | | | | 350 | | |
| Pro | Val | Thr | Pro | Tyr | Arg | Leu | His | Val | Leu | Cys | Gln | Gly | Trp | His | Tyr |
| | | 355 | | | | | 360 | | | | | 365 | | | |
| Leu | Ala | Tyr | Asp | Trp | His | Trp | Thr | Thr | Asp | Arg | Ser | Val | Gly | Asp | Asn |
| | 370 | | | | | 375 | | | | | 380 | | | | |
| Ser | Ser | Asp | Leu | Ser | Asn | Val | Ala | Val | Ile | Asp | Gly | Asn | Arg | Val | Leu |
| 385 | | | | | 390 | | | | | 395 | | | | | 400 |
| Val | Thr | Val | Phe | Arg | Gln | Thr | Val | Val | Pro | Pro | Met | Cys | Thr | Tyr |
| | | | | 405 | | | | | 410 | | | | | 415 | |
| Gln | Leu | Leu | Phe | Pro | His | Pro | Val | Asn | Gln | Val | Thr | Phe | Leu | Ala | His |
| | | | 420 | | | | | 425 | | | | | 430 | | |
| Pro | Gln | Lys | Ser | Asn | Asp | Leu | Ala | Val | Leu | Asp | Ala | Ser | Asn | Gln | Ile |
| | | 435 | | | | | 440 | | | | | 445 | | | |
| Ser | Val | Tyr | Lys | Cys | Gly | Asp | Cys | Pro | Ser | Ala | Asp | Pro | Thr | Val | Lys |
| | 450 | | | | | 455 | | | | | 460 | | | | |
| Leu | Gly | Ala | Val | Gly | Gly | Ser | Gly | Phe | Lys | Val | Cys | Leu | Arg | Thr | Pro |
| 465 | | | | | 470 | | | | | 475 | | | | | 480 |
| His | Leu | Glu | Lys | Arg | Tyr | Lys | Ile | Gln | Phe | Glu | Asn | Asn | Glu | Asp | Gln |
| | | | | 485 | | | | | 490 | | | | | 495 | |
| Asp | Val | Asn | Pro | Leu | Lys | Leu | Gly | Leu | Leu | Thr | Trp | Ile | Glu | Glu | Asp |
| | | | 500 | | | | | 505 | | | | | 510 | | |
| Val | Phe | Leu | Ala | Val | Ser | His | Ser | Glu | Phe | Ser | Pro | Arg | Ser | Val | Ile |
| | | 515 | | | | | 520 | | | | | 525 | | | |
| His | His | Leu | Thr | Ala | Ala | Ser | Ser | Glu | Met | Asp | Glu | Glu | His | Gly | Gln |
| | 530 | | | | | 535 | | | | | 540 | | | | |
| Leu | Asn | Val | Ser | Ser | Ser | Ala | Ala | Val | Asp | Gly | Val | Ile | Ile | Ser | Leu |

-continued

```
        545                     550                     555                     560
Cys Cys Asn Ser Lys Thr Lys Ser Val Val Leu Gln Leu Ala Asp Gly
                565                     570                     575
Gln Ile Phe Lys Tyr Leu Trp Glu Ser Pro Ser Leu Ala Ile Lys Pro
                580                     585                     590
Trp Lys Asn Ser Gly Gly Phe Pro Val Arg Phe Pro Tyr Pro Cys Thr
                595                     600                     605
Gln Thr Glu Leu Ala Met Ile Gly Glu Glu Glu Cys Val Leu Gly Leu
        610                     615                     620
Thr Asp Arg Cys Arg Phe Phe Ile Asn Asp Ile Glu Val Ala Ser Asn
625                     630                     635                     640
Ile Thr Ser Phe Ala Val Tyr Asp Glu Phe Leu Leu Leu Thr Thr His
                645                     650                     655
Ser His Thr Cys Gln Cys Phe Cys Leu Arg Asp Ala Ser Phe Lys Thr
                660                     665                     670
Leu Gln Ala Gly Leu Ser Ser Asn His Val Ser His Gly Glu Val Leu
                675                     680                     685
Arg Lys Val Glu Arg Gly Ser Arg Ile Val Thr Val Val Pro Gln Asp
        690                     695                     700
Thr Lys Leu Val Leu Gln Met Pro Arg Gly Asn Leu Glu Val Val His
705                     710                     715                     720
His Arg Ala Leu Val Leu Ala Gln Ile Arg Lys Trp Leu Asp Lys Leu
                        725                     730                     735
Met Phe Lys Glu Ala Phe Glu Cys Met Arg Lys Leu Arg Ile Asn Leu
                740                     745                     750
Asn Pro Ile Tyr Asp His Asn Pro Lys Val Phe Leu Gly Asn Val Glu
                755                     760                     765
Thr Phe Ile Lys Gln Ile Asp Ser Val Asn His Ile Asn Leu Phe Phe
        770                     775                     780
Thr Glu Leu Lys Glu Glu Asp Val Thr Lys Thr Met Tyr Pro Ala Pro
785                     790                     795                     800
Val Thr Ser Ser Val Tyr Leu Ser Arg Asp Pro Asp Gly Asn Lys Ile
                        805                     810                     815
Asp Leu Val Cys Asp Ala Met Arg Ala Val Met Glu Ser Ile Asn Pro
                820                     825                     830
His Lys Tyr Cys Leu Ser Ile Leu Thr Ser His Val Lys Lys Thr Thr
                835                     840                     845
Pro Glu Leu Glu Ile Val Leu Gln Lys Val His Glu Leu Gln Gly Asn
        850                     855                     860
Ala Pro Ser Asp Pro Asp Ala Val Ser Ala Glu Glu Ala Leu Lys Tyr
865                     870                     875                     880
Leu Leu His Leu Val Asp Val Asn Glu Leu Tyr Asp His Ser Leu Gly
                        885                     890                     895
Thr Tyr Asp Phe Asp Leu Val Leu Met Val Ala Glu Lys Ser Gln Lys
                900                     905                     910
Asp Pro Lys Glu Tyr Leu Pro Phe Leu Asn Thr Leu Lys Lys Met Glu
                915                     920                     925
Thr Asn Tyr Gln Arg Phe Thr Ile Asp Lys Tyr Leu Lys Arg Tyr Glu
        930                     935                     940
Lys Ala Ile Gly His Leu Ser Lys Cys Gly Pro Glu Tyr Phe Pro Glu
945                     950                     955                     960
Cys Leu Asn Leu Ile Lys Asp Lys Asn Leu Tyr Asn Glu Ala Leu Lys
                        965                     970                     975
```

-continued

| | | | | | | | | | | | | | | |
|---|---|---|---|---|---|---|---|---|---|---|---|---|---|---|
| Leu | Tyr | Ser | Pro 980 | Ser | Ser | Gln | Gln 985 | Tyr | Gln | Asp | Ile | Ser | Ile 990 | Ala | Tyr |
| Gly | Glu | His 995 | Leu | Met | Gln | Glu | His 1000 | Met | Tyr | Glu | Pro | Ala 1005 | Gly | Leu | Met |
| Phe | Ala | Arg 1010 | Cys | Gly | Ala | His 1015 | Glu | Lys | Ala | Leu | Ser | Ala 1020 | Phe | Leu | Thr |
| Cys 1025 | Gly | Asn | Trp | Lys 1030 | Gln | Ala | Leu | Cys | Val 1035 | Ala | Ala | Gln | Leu | Asn 1040 | Phe |
| Thr | Lys | Asp | Gln | Leu 1045 | Val | Gly | Leu | Gly | Arg 1050 | Thr | Leu | Ala | Gly | Lys 1055 | Leu |
| Val | Glu | Gln | Arg 1060 | Lys | His | Ile | Asp 1065 | Ala | Ala | Met | Val | Leu 1070 | Glu | Glu | Cys |
| Ala | Gln | Asp 1075 | Tyr | Glu | Glu | Ala 1080 | Val | Leu | Leu | Leu | Leu 1085 | Glu | Gly | Ala | Ala |
| Trp | Glu 1090 | Glu | Ala | Leu | Arg | Leu 1095 | Val | Tyr | Lys | Tyr | Asn 1100 | Arg | Leu | Asp | Ile |
| Ile 1105 | Glu | Thr | Asn | Val | Lys 1110 | Pro | Ser | Ile | Leu | Glu 1115 | Ala | Gln | Lys | Asn | Tyr 1120 |
| Met | Ala | Phe | Leu | Asp 1125 | Ser | Gln | Thr | Ala | Thr 1130 | Phe | Ser | Arg | His | Lys 1135 | Lys |
| Arg | Leu | Leu | Val 1140 | Val | Arg | Glu | Leu | Lys 1145 | Glu | Gln | Ala | Gln | Gln 1150 | Ala | Gly |
| Leu | Asp | Asp | Glu 1155 | Val | Pro | His | Gly 1160 | Gln | Glu | Ser | Asp | Leu 1165 | Phe | Ser | Glu |
| Thr | Ser | Ser 1170 | Val | Val | Ser | Gly 1175 | Ser | Glu | Met | Ser | Gly 1180 | Lys | Tyr | Ser | His |
| Ser 1185 | Asn | Ser | Arg | Ile | Ser 1190 | Ala | Arg | Ser | Ser | Lys 1195 | Asn | Arg | Arg | Lys | Ala 1200 |
| Glu | Arg | Lys | Lys | His 1205 | Ser | Leu | Lys | Glu | Gly 1210 | Ser | Pro | Leu | Glu | Asp 1215 | Leu |
| Ala | Leu | Leu | Glu 1220 | Ala | Leu | Ser | Glu | Val 1225 | Val | Gln | Asn | Thr | Glu 1230 | Asn | Leu |
| Lys | Asp | Glu | Val 1235 | Tyr | His | Ile | Leu 1240 | Lys | Val | Leu | Phe | Leu 1245 | Phe | Glu | Phe |
| Asp | Glu | Gln 1250 | Gly | Arg | Glu | Leu 1255 | Gln | Lys | Ala | Phe | Glu 1260 | Asp | Thr | Leu | Gln |
| Leu | Met 1265 | Glu | Arg | Ser | Leu 1270 | Pro | Glu | Ile | Trp | Thr 1275 | Leu | Thr | Tyr | Gln | Gln 1280 |
| Asn | Ser | Ala | Thr | Pro 1285 | Val | Leu | Gly | Pro | Asn 1290 | Ser | Thr | Ala | Asn | Ser 1295 | Ile |
| Met | Ala | Ser | Tyr | Gln 1300 | Gln | Gln | Lys | Thr 1305 | Ser | Val | Pro | Val | Leu 1310 | Asp | Ala |
| Glu | Leu | Phe 1315 | Ile | Pro | Pro | Lys | Ile 1320 | Asn | Arg | Arg | Thr | Gln 1325 | Trp | Lys | Leu |
| Ser | Leu | Leu 1330 | Asp | | | | | | | | | | | | |

IKAP NUCLEIC ACIDS

FIELD OF THE INVENTION

The field of this invention is proteins involved in cell signal transduction.

BACKGROUND

Cytokines trigger changes in gene expression by modifying the activity of otherwise latent transcription factors (Hill and Treisman, 1995). Nuclear factor κB (NF-κB) is a prominent example of how such an external stimulus is converted into an active transcription factor (Verma et al., 1995). The NF-κB system is composed of homo- and heterodimers of members of the Rel family of related transcription factors that control the expression of numerous immune and inflammatory response genes as well as important viral genes (Lenardo and Baltimore, 1989; Baeuerle and Henkel, 1994). The activity of NF-κB transcription factors is regulated by their subcellular localization (Verma et al., 1995). In most cell types, NF-κB is present as a heterodimer comprising of a 50 kDa and a 65 kDa subunit. This heterodimer is sequestered in the cytoplasm in association with IκBα a member of the IκB family of inhibitory proteins (Finco and Baldwin, 1995; Thanos and Maniatis, 1995; Verma et al., 1995). IκBα masks the nuclear localization signal of NF-κB and thereby prevents NF-κB nuclear translocation. Conversion of NF-κB into an active transcription factor that translocates into the nucleus and binds to cognate DNA sequences requires the phosphorylation and subsequent ubiquitin-dependent degradation of IκBα in the 26s proteasome. Signal-induced phosphorylation of IκBα occurs at serines 32 and 36. Mutation of one or both of these serines renders IκBα resistant to ubiquitination and proteolytic degradation (Chen et al., 1995); DiDonato, 1996 #370, Roff, 1996 #397.

The pleiotropic cytokines tumor necrosis factor (TNF) and interleukin- 1 (IL-1) are among the physiological inducers of IκB phosphorylation and subsequent NF-κB activation (Osborn et al., 1989; Beg et al., 1993). Although TNF and IL-1 initiate signaling cascades leading to NF-κB activation via distinct families of cell-surface receptors (Smith et al., 1994; Dinarello, 1996), both pathways utilize members of the TNF receptor-associated factor (TRAF) family of adaptor proteins as signal transducers (Rothe et al., 1995; Hsu et al., 1996; Cao et al., 1996b). TRAF proteins were originally found to associate directly with the cytoplasmic domains of several members of the TNF receptor family including the 75 kDa TNF receptor (TNFR2), CD40, CD30, and the lymphotoxin-β receptor (Rothe et al., 1994; Hu et al., 1994; Cheng et al., 1995; Mosialos et al., 1995; Song and Donner, 1995; Sato et al., 1995; Lee et al., 1996; Gedrich et al., 1996; Ansieau et al., 1996). In addition, TRAF proteins are recruited indirectly to the 55 kDa TNF receptor (TNFR1) by the adaptor protein TRADD (Hsu et al., 1996). Activation of NF-κB by TNF requires TRAF2 (Rothe et al., 1995; Hsu et al., 1996). TRAF5 has also been implicated in NF-κB activation by members of the TNF receptor family (Nakano et al., 1996); Ishida, 1996 #240. In contrast, TRAF6 participates in NF-κB activation by IL-1 (Cao et al., 1996b). Upon IL-1 treatment, TRAF6 associates with IRAK, a serine-threonine kinase that binds to the IL-1 receptor complex (Cao et al., 1996a); Huang, 1997 #400.

The NF-κB-inducing kinase (NIK) is a member of the MAP kinase kinase kinase (MAP3K) family that was identified as a TRAF2-interacting protein (Malinin et al., 1997). NIK activates NF-κB when overexpressed, and kinase-inactive mutants of NIK comprising its TRAF2-interacting C-terminal domain ($NIK_{(624-947)}$) or lacking two crucial lysine residues in its kinase domain ($NIK_{(KK429-430AA)}$) behave as dominant-negative inhibitors that suppress TNF-, IL-1-, and TRAF2-induced NF-κB activation (Malinin et al., 1997). Recently, NIK was found to associate with additional members of the TRAF family, including TRAF5 and TRAF6. Catalytically inactive mutants of NIK also inhibited TRAF5- and TRAF6-induced NF-κB activation, thus providing a unifying concept for NIK as a common mediator in the NF-κB signaling cascades triggered by TNF and IL-1 downstream of TRAFs. Recently two NIK-interacting protein designated characterized as novel human kinase IκB Kinases, IKK-α and IKK-β have been reported (Woronicz et al., 1997; Mercurio et al. 1997; Maniatis, 1997). Catalytically inactive mutants of IKK suppress NF-κB activation induced by TNF and IL-1 stimulation as well as by TRAF and NIK overexpression; transiently expressed IKK associates with endogenous IκBα complex; and IKK phosphorylates IκBα on serines 32 and 36.

Relevant Literature

Ansieau, S., et al. (1996). Proc. Natl. Acad. Sci. USA 93, 14053–14058.

Baeuerle, P. A., and Henkel, T. (1994). Annu. Rev. Immunol. 12, 141–179.

Beg, A. A., et al. (1993). Mol. Cell. Biol. 13, 3301–3310.

Cao, Z., Henzel, W. J., and Gao, X. (1996a). Science 271, 1128–1131.

Cao, Z., et al. (1996b). Nature 383, 443–446.

Chen, Z., et al. (1995). Genes Dev. 9, 1586–1597.

Cheng, G., et al. (1995). Science 267, 1494–1498.

Connelly, M. A., and Marcu, K. B. (1995). Cell. Mol. Biol. Res. 41, 537–549.

Dinarello, C. A. (1996). Biologic basis for interleukin-1 in disease. Blood 87, 2095–2147.

Fields, S., and Song, O. -k. (1989). Nature 340, 245–246.

Finco, T. S., and Baldwin, A. S. (1995). Immunity 3, 263–272.

Gedrich, R. W., et al. (1996). J. Biol. Chem. 271, 12852–12858.

Hill, C. S., and Treisman, R. (1995). Cell 80, 199–211.

Hsu, H., Shu, H. -B., Pan, M. -P., and Goeddel, D. V. (1996). Cell 84, 299–308.

Hu, H. M., et al. (1994). J. Biol. Chem. 269, 30069–30072.

Lee, S. Y., et al. (1996). Proc. Natl. Acad. Sci. USA 93, 9699–9703.

Lenardo, M., and Baltimore, D. (1989). Cell 58, 227–229.

Malinin, N. L., et al. (1997). Nature 385, 540–544.

Maniatis (1997) Science 278, 818.

Mercurio et al.(1997) Science 278, 860.

Mock et al. (1995). Genomics 27, 348–351.

Mosialos, G., et al. (1995). Cell 80, 389–399.

Nakano, H., et al. (1996). J. Biol. Chem. 271, 14661–14664.

Osborn, L., et al. (1989). Proc. Natl. Acad. Sci. USA 86, 2336–2340.

Rothe, M., Sarma, V., Dixit, V. M., and Goeddel, D. V. (1995). Science 269, 1424–1427.

Rothe, M., Wong, S. C., Henzel, W. J., and Goeddel, D. V. (1994). Cell 78, 681–692.

Sato, T., Irie, S., and Reed, J. C. (1995). FEBS Lett. 358, 113–118.

Schindler, U., and Baichwal, V. R. (1994). Mol. Cell. Biol. 14, 5820–5831.

Smith, C. A., Farrah, T., and Goodwin, R. G. (1994). Cell 76, 959–962.

Song, H. Y., and Donner, D. B. (1995). Biochem. J. 809, 825–829.

Thanos, D., and Maniatis, T. (1995). Cell 80, 529–532.
Woronicz et al., (1997) Science 278, 866.
Verma, I. M., et al. (1995). Genes Dev. 9, 2723–2735.

SUMMARY OF THE INVENTION

The invention provides methods and compositions relating to isolated IKAP polypeptides, related nucleic acids, polypeptide domains thereof having IKAP-specific structure and activity and modulators of IKAP function, particularly NIK binding activity. IKAP polypeptides can regulate NFκB activation and hence provide important regulators of cell finction. The polypeptides may be produced recombinantly from transformed host cells from the subject IKAP polypeptide encoding nucleic acids or purified from mammalian cells. The invention provides isolated IKAP hybridization probes and primers capable of specifically hybridizing with the disclosed IKAP gene, IKAP-specific binding agents such as specific antibodies, and methods of making and using the subject compositions in diagnosis (e.g. genetic hybridization screens for IKAP transcripts), therapy (e.g. IKAP inhibitors to inhibit TNF signal transduction) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

Figure 1:
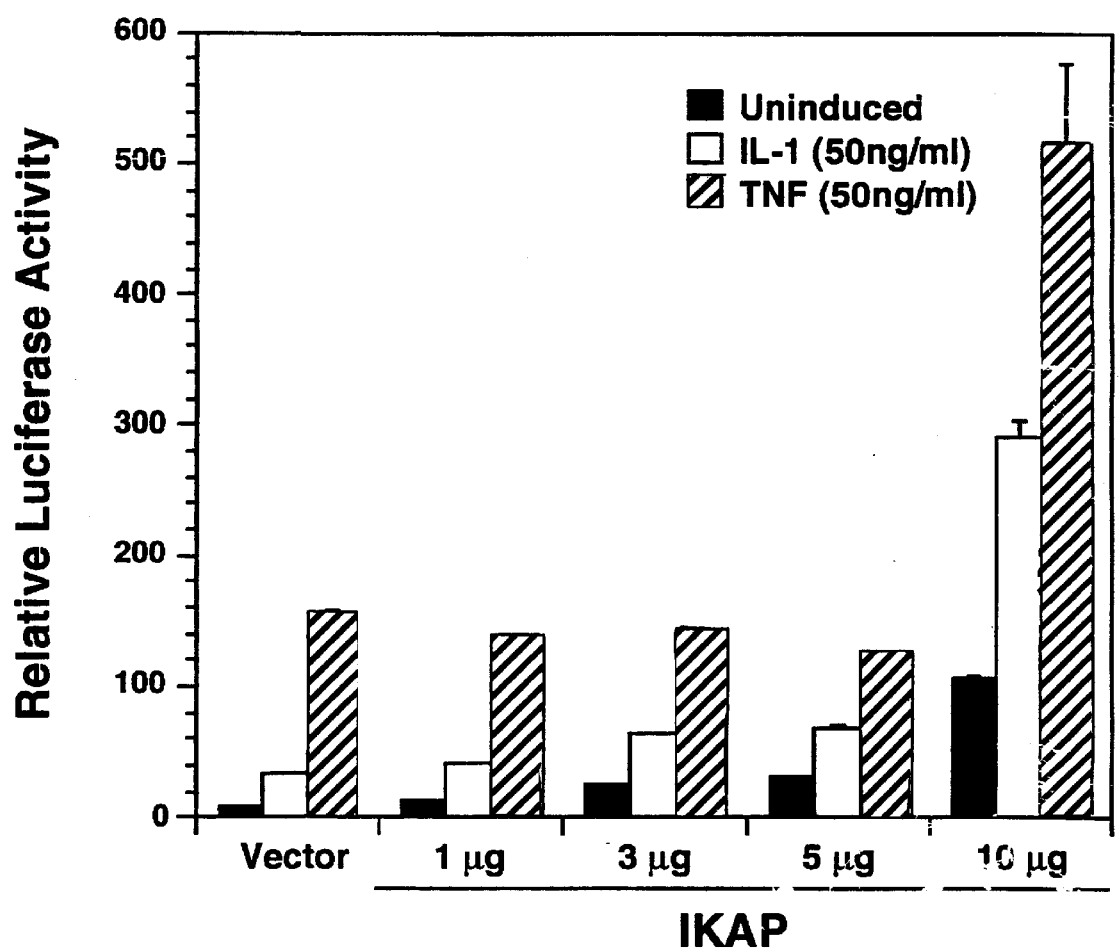
FIG. 1. IKAP polypeptides activate NFκB.

The nucleotide sequence of a natural cDNA encoding a human IKAP polypeptide is shown as SEQ ID NO:1, and the full conceptual translate is shown as SEQ ID NO:2. The IKAP polypeptides of the invention include one or more functional domains of SEQ ID NO:2, which domains comprise at least 8, preferably at least 16, more preferably at least 32, most preferably at least 64 contiguous residues of SEQ ID NO:2 and have human IKAP-specific amino acid sequence and activity. IKAP domain specific activities include NIK-binding or binding inhibitory activity, NFκB-binding or binding inhibitory activity and IKAP specific immunogenicity and/or antigenicity.

IKAP-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an IKAP polypeptide with a binding target is evaluated. The binding target may be a natural intracellular binding target such as an IKAP binding target, a IKAP regulating protein or other regulator that directly modulates IKAP activity or its localization; or non-natural binding target such a specific immune protein such as an antibody, or an IKAP specific agent such as those identified in screening assays such as described below. IKAP-binding specificity may assayed by binding equilibrium constants (usually at least about $10^7 M^{-1}$, preferably at least about $10^8 M^{-1}$, more preferably at least about $10^9 M^{-1}$), by NFκB reporter expression, by the ability of the subject polypeptide to function as negative mutants in IKAP-expressing cells, to elicit IKAP specific antibody in a heterologous host (e.g a rodent or rabbit), etc.

For example, deletion mutagenesis is used to defined functional IKAP) domains which activate NFκB expression or function as dominant/negative mutants in IKAP-mediated NFκB activation assays. See, e.g. Table 1.

TABLE 1

Exemplary IKAP deletion mutants defining IKAP functional domains.

| Mutant | Sequence | NFκB | Dom/Neg |
|---|---|---|---|
| ΔN1 | SEQ ID NO:2, residues 42–1332 | + | − |
| ΔN2 | SEQ ID NO:2, residues 142–1332 | + | − |
| ΔN3 | SEQ ID NO:2, residues 242–1332 | + | − |
| ΔN4 | SEQ ID NO:2, residues 342–1332 | + | − |
| ΔN5 | SEQ ID NO:2, residues 442–1332 | + | − |
| ΔC1 | SEQ ID NO:2, residues 1–923 | − | + |
| ΔC2 | SEQ ID NO:2, residues 1–441 | − | |
| ΔC3 | SEQ ID NO:2, residues 1–241 | − | |
| ΔC4 | SEQ ID NO:2, residues 1–241 | − | |

In a particular embodiment, the subject domains provide IKAP-specific antigens and/or immunogens, especially when coupled to carrier proteins. For example, peptides corresponding to IKAP- and human IKAP-specific domains are covalently coupled to keyhole limpet antigen (KLH) and the conjugate is emulsified in Freunds complete adjuvant. Laboratory rabbits are immunized according to conventional protocol and bled. The presence of IKAP-specific antibodies is assayed by solid phase immunosorbant assays using immobilized IKAP polypeptides of SEQ ID NO:2, see, e.g. Table 2.

TABLE 2

Immunogenic IKAP polypeptides eliciting IKAP-specific rabbit polyclonal antibody: IKAP polypeptide-KLH conjugates immunized per protocol described above.

| IKAP Polypeptide Sequence | Immunogenicity |
|---|---|
| SEQ ID NO:2, residues 1–10 | +++ |
| SEQ ID NO:2, residues 29–41 | +++ |
| SEQ ID NO:2, residues 75–87 | +++ |
| SEQ ID NO:2, residues 92–109 | +++ |
| SEQ ID NO:2, residues 132–141 | +++ |
| SEQ ID NO:2, residues 192–205 | +++ |
| SEQ ID NO:2, residues 258–269 | +++ |
| SEQ ID NO:2, residues 295–311 | +++ |
| SEQ ID NO:2, residues 316–330 | +++ |
| SEQ ID NO:2, residues 373–382 | +++ |
| SEQ ID NO:2, residues 403–422 | +++ |
| SEQ ID NO:2, residues 474–485 | +++ |
| SEQ ID NO:2, residues 561–576 | +++ |
| SEQ ID NO:2, residues 683–697 | +++ |
| SEQ ID NO:2, residues 768–777 | +++ |
| SEQ ID NO:2, residues 798–813 | +++ |
| SEQ ID NO:2, residues 882–894 | +++ |
| SEQ ID NO:2, residues 934–946 | +++ |
| SEQ ID NO:2, residues 1054–1067 | +++ |
| SEQ ID NO:2, residues 1181–1192 | +++ |
| SEQ ID NO:2, residues 1273–1282 | +++ |
| SEQ ID NO:2, residues 1283–1294 | +++ |
| SEQ ID NO:2, residues 1295–1312 | +++ |
| SEQ ID NO:2, residues 1313–1332 | +++ |

The claimed IKAP polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The IKAP polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, N.Y.) or that are otherwise known in the art.

The invention provides binding agents specific to IKAP polypeptides, preferably the claimed IKAP polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel IKAP-specific binding agents include IKAP-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate IKAP function, e.g. IKAP-dependent transcriptional activation.

Accordingly, the invention provides methods for modulating signal transduction involving NFκB in a cell comprising the step of modulating IKAP activity. The cell may reside in culture or in situ, i.e. within the natural host. For diagnostic uses, the inhibitors or other IKAP binding agents are frequently labeled, such as with fluorescent, radioactive, chemiluminescent, or other easily detectable molecules, either conjugated directly to the binding agent or conjugated to a probe specific for the binding agent. Exemplary inhibitors include nucleic acids encoding dominant/negative mutant forms of IKAP, as described above, etc.

The amino acid sequences of the disclosed IKAP polypeptides are used to back-translate IKAP polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural IKAP-encoding nucleic acid sequences ("GCG" software, Genetics Computer Group, Inc, Madison Wis.). IKAP-encoding nucleic acids used in IKAP-expression vectors and incorporated into recombinant host cells, e.g. for expression and screening, transgenic animals, e.g. for functional studies such as the efficacy of candidate drugs for disease associated with IKAP-modulated cell function, etc.

The invention also provides nucleic acid hybridization probes and replication/amplification primers having a IKAP cDNA specific sequence comprising at least 12, preferably at least 24, more preferably at least 36 and most preferably at least contiguous 96 bases of a strand of SEQ ID NO:1 sufficient to specifically hybridize with a second nucleic acid comprising the complementary strand of SEQ ID NO:1. Demonstrating specific hybridization generally requires stringent conditions, for example, hybridizing in a buffer comprising 30% formamide in 5×SSPE (0.18M NaCl, 0.01M NaPO$_4$, pH7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C.

TABLE 3

Exemplary IKAP nucleic acids which hybridize with a strand of SEQ ID NO: 1 under Conditions I and/or II.

| IKAP Nucleic Acids | Hybridization |
|---|---|
| SEQ ID NO:1, nucleotides 1–47 | + |
| SEQ ID NO:1, nucleotides 58–99 | + |
| SEQ ID NO:1, nucleotides 95–138 | + |
| SEQ ID NO:1, nucleotides 181–220 | + |
| SEQ ID NO:1, nucleotides 261–299 | + |
| SEQ ID NO:1, nucleotides 274–315 | + |
| SEQ ID NO:1, nucleotides 351–389 | + |
| SEQ ID NO:1, nucleotides 450–593 | + |
| SEQ ID NO:1, nucleotides 524–546 | + |
| SEQ ID NO:1, nucleotides 561–608 | + |
| SEQ ID NO:1, nucleotides 689–727 | + |
| SEQ ID NO:1, nucleotides 808–837 | + |
| SEQ ID NO:1, nucleotides 938–1001 | + |
| SEQ ID NO:1, nucleotides 1205–1254 | + |
| SEQ ID NO:1, nucleotides 1855–1907 | + |
| SEQ ID NO:1, nucleotides 2910–2953 | + |
| SEQ ID NO:1, nucleotides 3967–3999 | + |

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, or requisite fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of IKAP genes and gene transcripts and in detecting or amplifying nucleic acids encoding additional IKAP homologs and structural analogs. In diagnosis, IKAP hybridization probes find use in identifying wild-type and mutant IKAP alleles in clinical and laboratory samples. Mutant alleles are used to generate allele-specific oligonucleotide (ASO) probes for high-throughput clinical diagnoses. In therapy, therapeutic IKAP nucleic acids are used to modulate cellular expression or intracellular concentration or availability of active IKAP.

The invention provides efficient methods of identifying agents, compounds or lead compounds for agents active at the level of a IKAP modulatable cellular function. Generally, these screening methods involve assaying for compounds which modulate IKAP interaction with a natural IKAP binding target, such as NIK A wide variety of assays for binding agents are provided including labeled in vitro protein—protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an IKAP polypeptide, which may be part of a fusion product with another peptide or polypeptide, e.g. a tag for detection or anchoring, etc. The assay mixtures comprise a natural intracellular IKAP binding target. While native full-length binding targets may be used, it is frequently preferred to use portions (e.g. peptides) thereof so long as the portion provides binding affinity and avidity to the subject IKAP polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the IKAP polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the IKAP polypeptide and one or more binding targets is detected by any convenient way. A difference in the binding affinity of the IKAP polypeptide to the target in the absence of the agent as compared with the binding affinity in the presence of the agent indicates that the agent modulates the binding of the IKAP polypeptide to the IKAP binding target. Analogously, in the cell-based assay also described below, a difference in IKAP-dependent transcriptional activation in the presence and absence of an agent indicates the agent modulates IKAP function. A difference, as used herein, is statistically significant and preferably represents at least a 50%, more preferably at least a 90% difference.

The following experimental section and examples are offered by way of illustration and not by way of limitation.

EXAMPLES

1. Protocol for Cell-Based IKAP-NIK Interaction assay

IKAP has been identified as a NIK-interacting protein by coprecipitation assay: 293 cells are transfected with mammalian expression vectors encoding Flag-tagged NIK and Myc-tagged IKAP respectively. After 48 hours, cells are collected, washed twice with phosphate-buffered saline and lysed for 30 min at 4° C. in 0.5 ml of lysis buffer ( 50 mM HEPES pH 7.6, 100 mM NaCl, 1% NP-40, 1 mM EDTA, 10% glycerol) containing phosphatase and protease inhibitors. Cellular debris are removed by centrifugation at 10,000×g for 10 min twice. The NaCl concentration of the cell lysates is increased to 250 MM. The cell lysates are incubated for 1 hour on ice with 1 82 g of anti-Flag monoclonal antibody or control mouse IgGI antibody, and an additional hour at 4° C. with 15 $\mu$l of protein G-agarose beads. The beads are then collected, and washed four times with 1 ml of lysis buffer containing 250 mM NaCl. The bound proteins are eluted, fractionated by SDS-PAGE and analyzed by western blotting using anti-Myc or anti-Flag polyclonal antibodies. The inmunoblot is developed with horseradish peroxidase-coupled goat anti-rabbit immunoglobin as secondary antibody and visualized using the Enhanced Chemoluminescence (ECL) Detection System.

2. Protocol for Cell-Based NF-κB Reporter Assay

IKAP can trans-activate NF-κB reporter constructs when overexpressed in 293 cells or HeLa cells. 293 cells are transfected using the calcium phosphate precipitation method with a plasmid encoding a 6 NF-κB-luciferase reporter construct and various amounts of expression vector encoding IKAP. After 36–48 hours, cells are left untreated or treated with IL-1 (10–50 ng/ml) or TNF (50–100 ng) for 6 hours prior to harvest. Cells are lysed and luciferase activity measured using the luciferase assay kit (Promega). The luciferase activity in each transfection is normalized by co-transfecting a pRSV-β gal control vector.

3. Protocol for high throughput in vitro IKAP-NIK binding assay.

A. Reagents:
Neutralite Avidin: 20 $\mu$g/ml in PBS.
Blocking buffer: 5% BSA, 0.5% Tween 20 in PBS; 1 hour at room temperature.
Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.
$^{33}$IKAP polypeptide 10×stock: $10^{-8}$–$10^{-6}$M "cold" IKAP supplemented with 200,000–250,000 cpm of labeled IKAP (Beckman counter). Place in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2mM NaVO$_3$ (Sigma #S-6508) in 10 ml of PBS.
NIK: $10^{-7}$–$10^{-5}$M biotinylated NIK in PBS.

B. Preparation of assay plates:
Coat with 120 $\mu$l of stock N-Avidin per well overnight at 4° C.
Wash 2 times with 200 $\mu$l PBS.
Block with 150 $\mu$l of blocking buffer.
Wash 2 times with 200 $\mu$l PBS.

C. Assay:
Add 40 $\mu$l assay buffer/well.
Add 10 $\mu$l compound or extract.
Add 10 $\mu$l $^{33}$P-IKAP (20–25,000 cpm/0.1–10 pmoles/well=$10^{-9}$–$10^{-7}$M final conc).
Shake at 25° C. for 15 minutes.
Incubate additional 45 minutes at 25° C.
Add 40 $\mu$M biotinylated NIK (0.1–10 pmoles/40 ul in assay buffer)
Incubate 1 hour at room temperature.
Stop the reaction by washing 4 times with 200 $\mu$M PBS.
Add 150 $\mu$M scintillation cocktail.
Count in Topcount.

D. Controls for all assays (located on each plate):
a. Non-specific binding
b. Soluble (non-biotinylated NIK) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinant nucleic acid comprising a coding region encoding SEQ ID NO:2 or fragment thereof selected from the group consisting of: residues 1–10, 132–141, 192–205, 258–269, 295–311, 373–382, 403–422, 474–485, 683–697, and 1054–1067, said coding region flanked by fewer than 2 kb of native flanking sequence.

2. A nucleic acid according to claim 1 encoding SEQ ID NO:2 residues 1–10.

3. A nucleic acid according to claim 1 encoding SEQ ID NO:2 residues 132–141.

4. A nucleic acid according to claim 1 encoding SEQ ID NO:2 residues 192–205.

5. A nucleic acid according to claim 1 encoding SEQ ID NO:2 residues 258–269.

6. A nucleic acid according to claim 1 encoding SEQ ID NO:2 residues 295–311.

7. A nucleic acid according to claim 1 encoding SEQ ID NO:2 residues 373–382.

8. A nucleic acid according to claim 1 encoding SEQ ID NO:2 residues 403–422.

9. A nucleic acid according to claim 1 encoding SEQ ID NO:2 residues 474–485.

10. A nucleic acid according to claim 1 encoding SEQ ID NO:2 residues 683–697.

11. A nucleic acid according to claim 1 encoding SEQ ID NO:2 residues 1054–1067.

12. A nucleic acid according to claim 1 encoding SEQ ID NO:2.

13. A recombinant nucleic acid comprising the nucleotide sequence of SEQ ID NO:1, a complement thereof, a fragment of SEQ ID NO:1 selected from the group consisting of nucleotides 1–47, 58–99, 181–220, 351–389, 450–593, 524–546, 561–608, 689–727, 1205–1254, or a complement thereof, said nucleotide sequence flanked by fewer than 2 kb of native flanking sequence.

14. A nucleic acid according to claim 13 comprising a nucleotide sequence of a fragment of SEQ ID NO:1, wherein said fragment is nucleotides 1–47 of SEQ ID NO:1, or a complement thereof.

15. A nucleic acid according to claim 13 comprising a nucleotide sequence of a fragment of SEQ ID NO:1, wherein said fragment is nucleotides 58–99 of SEQ ID NO:1, or a complement thereof.

16. A nucleic acid according to claim 13 comprising a nucleotide sequence of a fragment of SEQ ID NO:1, wherein said fragment is nucleotides 181–220 of SEQ ID NO:1, or a complement thereof.

17. A nucleic acid according to claim 13 comprising a nucleotide sequence of a fragment of SEQ ID NO:1, wherein said fragment is nucleotides 351–389 of SEQ ID NO:1, or a complement thereof.

18. A nucleic acid according to claim 13 comprising a nucleotide sequence of a fragment of SEQ ID NO:1, wherein said fragment is nucleotides 450–593 of SEQ ID NO:1, or a complement thereof.

19. A nucleic acid according to claim 13 comprising a nucleotide sequence of a fragment of SEQ ID NO:1, wherein said fragment is nucleotides 524–546 of SEQ ID NO:1, or a complement thereof.

20. A nucleic acid according to claim 13 comprising a nucleotide sequence of a fragment of SEQ ID NO:1, wherein said fragment is nucleotides 561–608 of SEQ ID NO:1, or a complement thereof.

21. A nucleic acid according to claim 13 comprising a nucleotide sequence of a fragment of SEQ ID NO:1, wherein said fragment is nucleotides 689–727 of SEQ ID NO:1, or a complement thereof.

22. A nucleic acid according to claim 13 comprising a nucleotide. sequence of a fragment of SEQ ID NO:1, wherein said fragment is nucleotides 1205–1254 of SEQ ID NO:1, or a complement thereof.

23. A nucleic acid according to claim 13 comprising a nucleotide sequence of SEQ ID NO:1, or a complement thereof.

24. A cell comprising a recombinant nucleic acid:
(a) comprising a coding region encoding SEQ ID NO:2 or fragment thereof selected from the group consisting of: residues 1–10, 132–141, 192–205, 258–269, 295–311, 373–382, 403–422, 474–485, 683–697 and 1054–1067, said coding region flanked by fewer than 2 kb of native flanking sequence; or
(b) comprising the nucleotide sequence of SEQ ID NO:1, a complement thereof, a fragment of SEQ ID NO:1 selected from the group consisting of nucleotides 1–47, 58–99, 181–220, 351–389, 450–593, 524–546, 561–608, 689–727, 1205–1254, or a complement thereof, said nucleotide sequence flanked by fewer than 2 kb of native flanking sequence.

25. A recombinant nucleic acid consisting of:
(a) a fragment of a coding region encoding SEQ ID NO:2 selected from the group consisting of: residues 29–41, 75–87, 92–109, 316–330, 561–576, 768–777, 798–813, 1181–1192, 1273–1282, 1283–1294, 1295–1312 and 1313–1332; or
(b) the nucleotide sequence of a fragment of SEQ ID NO:1 selected from the group consisting of nucleotides 95–138, 261–299, 274–315, 808–837, 938–1001, 1855–1907, 2910–2953 and 3967–3999, or a complement thereof, said nucleotide sequence flanked by fewer than 2 kb of native flanking sequence.

26. A cell comprising a recombinant nucleic acid of claim 25.

27. A nucleic acid according to claim 25 encoding SEQ ID NO:2 residues 29–41.

28. A nucleic acid according to claim 25 encoding SEQ ID NO:2 residues 75–87.

29. A nucleic acid according to claim 25 encoding SEQ ID NO:2 residues 92–109.

30. A nucleic acid according to claim 25 encoding SEQ ID NO:2 residues 316–330.

31. A nucleic acid according to claim 25 encoding SEQ ID NO:2 residues 561–576.

32. A nucleic acid according to claim 25 encoding SEQ ID NO:2 residues 768–777.

33. A nucleic acid according to claim 25 encoding SEQ ID NO:2 residues 798–813.

34. A nucleic acid according to claim 25 encoding SEQ ID NO:2 residues 1181–1192.

35. A nucleic acid according to claim 25 encoding SEQ ID NO:2 residues 1273–1282.

36. A nucleic acid according to claim 25 encoding SEQ ID NO:2 residues 1283–1294.

37. A nucleic acid according to claim 25 encoding SEQ ID NO:2 residues 1295–1312.

38. A nucleic acid according to claim 25 encoding SEQ ID NO:2 residues 1313–1332.

39. A nucleic acid according to claim 25 consisting of nucleotides 95–138 of SEQ ID NO:1.

40. A nucleic acid according to claim 25 consisting of nucleotides 261–299 of SEQ ID NO:1, or the complement thereof.

41. A nucleic acid according to claim 25 consisting of nucleotides 274–315 of SEQ ID NO:1, or the complement thereof.

42. A nucleic acid according to claim 25 consisting of nucleotides 808–837 of SEQ ID NO:1, or the complement thereof.

43. A nucleic acid according to claim 25 consisting of nucleotides 938–1001 of SEQ ID NO:1, or the complement thereof.

44. A nucleic acid according to claim 25 consisting of nucleotides 1855–1907 of SEQ ID NO:1, or the complement thereof.

45. A nucleic acid according to claim 25 consisting of nucleotides 2910–2953 of SEQ ID NO:1, or the complement thereof.

46. A nucleic acid according to claim 25 consisting of nucleotides 3967–3999 of SEQ ID NO:1, or the complement thereof.

* * * * *